(12) United States Patent
Robinson

(10) Patent No.: US 10,457,948 B2
(45) Date of Patent: Oct. 29, 2019

(54) BIOPHARMACEUTICAL PRODUCTION METHOD

(71) Applicant: University of Kent, Canterbury (GB)

(72) Inventor: Colin Robinson, Canterbury (GB)

(73) Assignee: University of Kent, Canterbury (GB)

( * ) Notice: Subject to any disclaimer, the term of this patent is extended or adjusted under 35 U.S.C. 154(b) by 0 days.

(21) Appl. No.: 15/524,783

(22) PCT Filed: Nov. 6, 2015

(86) PCT No.: PCT/GB2015/053371
§ 371 (c)(1),
(2) Date: May 5, 2017

(87) PCT Pub. No.: WO2016/071707
PCT Pub. Date: May 12, 2016

(65) Prior Publication Data
US 2017/0321221 A1    Nov. 9, 2017

(30) Foreign Application Priority Data
Nov. 7, 2014 (GB) .................................. 1419899.8

(51) Int. Cl.

| | |
|---|---|
| C12N 15/70 | (2006.01) |
| C12P 21/02 | (2006.01) |
| C12N 1/20 | (2006.01) |
| C12N 15/62 | (2006.01) |
| C12N 9/16 | (2006.01) |
| C07K 14/245 | (2006.01) |

(52) U.S. Cl.
CPC ............ *C12N 15/70* (2013.01); *C07K 14/245* (2013.01); *C12N 1/20* (2013.01); *C12N 9/16* (2013.01); *C12N 15/62* (2013.01); *C12N 15/625* (2013.01); *C12P 21/02* (2013.01); *C07K 2319/034* (2013.01)

(58) Field of Classification Search
None
See application file for complete search history.

(56) References Cited

U.S. PATENT DOCUMENTS

2003/0219870 A1*  11/2003  Georgiou ........... C12N 15/1037
                                                         506/2

FOREIGN PATENT DOCUMENTS

| MX | NL06000069 | 10/2008 |
|---|---|---|
| WO | 03/083056 | 10/2003 |
| WO | 2009021548 | 2/2009 |
| WO | 2014/030780 | 2/2014 |

OTHER PUBLICATIONS

Jorgensen, Jens Otto Lunde. Chapter 20—Growth Hormone. 1997. Principles of Medical Biology. vol. 10B, Molecular and Cellular Endocrinology, pp. 451-466. (Year: 1997).*

Khodabandeh et al. Purification of large quantities of biologically active recombinant human growth hormone. Oct. 2003. Iranian Journal of Biotechnology. vol. 1, No. 4, pp. 207-212. (Year: 2003).*

Alanen et al. "Efficient Export of Human Growth Hormone, Interferon [Alpha]2b and Antibody Fragments to the Periplasm by the *Escherichia coli* Tat Pathway in the Absence of Prior Disulfide Bond Formation", Biochimica Et Biophysica Acta. Molecular Cell Research, 2014, vol. 1853, No. 3, pp. 756-763.

Duncan et al. "Identification of SPQR Domain Amino Acids Important for Septal Localization, Peptidoglycan Binding, and a Disulfide Bond in the Cell Division Protein FTSN", Journal of Bacteriology, 2013, vol. 195, No. 23, pp. 5308-5315.

Fisher et al. "Efficient Isolation of Soluble Intracellular Single-Chain Antibodies Using the Twin-Arginine Translocation Machinery", Journal of Molecular Biology, Academic Press, United Kingdom, 2009, vol. 385, No. 1, pp. 299-311.

International Search Report and Written Opinion, for International Patent Application No. PCT/GB2015/053371, dated Jan. 18, 2016, 13 pages.

Karlsson et al. "Engineering Antibody Fitness and Function Using Membrane-Anchored Display of Correctly Folded Proteins", Journal of Molecular Biology, 2011, vol. 416, No. 1, pp. 94-107.

Medina-Rivero et al. "Modified Penicillin Acylase Signal Peptide Allows the Periplasmic Production of Soluble Human Interferon-[Gamma] But Not of Soluble Human Interleukin-2 by the Tat Pathway in *Escherichia coli*", Biotechnology Letters, Springer Netherlands, Dordrecht, 2007, vol. 29, No. 9, pp. 1369-1374.

Richter et al. "Functional Tat Transport of Unstructured, Small, Hydrophilic Proteins", Journal of Biological Chemistry, 2007, vol. 282, No. 46, pp. 33257-33264.

Robinson et al. "Transport and Proofreading of Proteins by the Twin-Arginine Translocation (Tat) System in Bacteria", Biochimica ET Biophysica Acta (Bba)—Biomembranes, Elsevier, Amsterdam, NL, 2010, vol. 1808, No. 3, pp. 876-884.

Soares et al. "Periplasmic, Expression of Human Growth Hormone via Plasmid Vectors Containing the PL Promoter: Use of HPLC for Product Quantification", Protein Engineering, Design and Selection, 2003, vol. 16, No. 12, pp. 1131-1138.

Waraho-Zhmayev et al. "Optimizing Recombinant Antibodies for Intracellular Function Using Hitchhiker-Mediated Survival Selection", Protein Engineering, Design and Selection, 2014, vol. 27, No. 10, pp. 1-10.

Waraho et al. "Versatile Selection Technology for Intracellular Protein-Protein Interactions Mediated by a Unique Bacterial Hitchhiker Transport Mechanism", Proceedings of the National Academy of Sciences, 2009, vol. 106, No. 10, pp. 3692-3697.

* cited by examiner

*Primary Examiner* — Channing S Mahatan
(74) *Attorney, Agent, or Firm* — Morgan, Lewis & Bockius LLP

(57) ABSTRACT

The present invention resides in a method for the manufacture of a disulphide-requiring biopharmaceutical having an element of at least tertiary structure using wild type *E. coli*.

7 Claims, 5 Drawing Sheets

Figure 1:
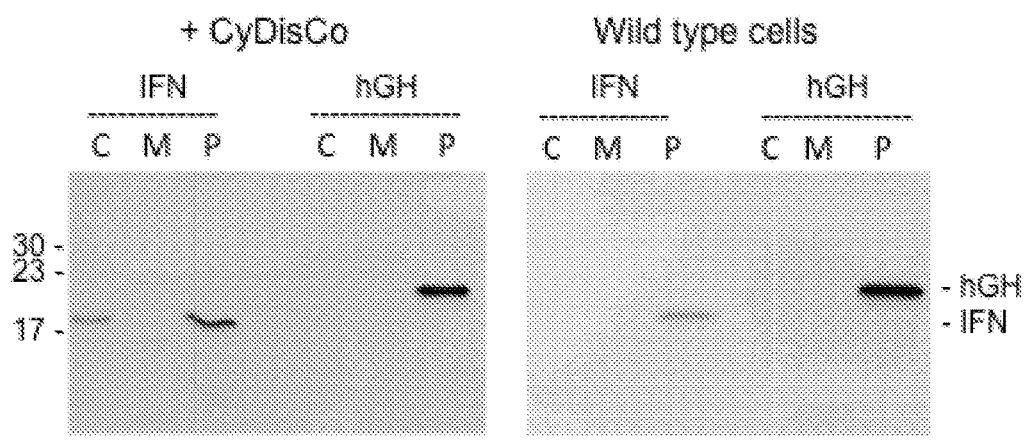

Specification includes a Sequence Listing.

Figure 3
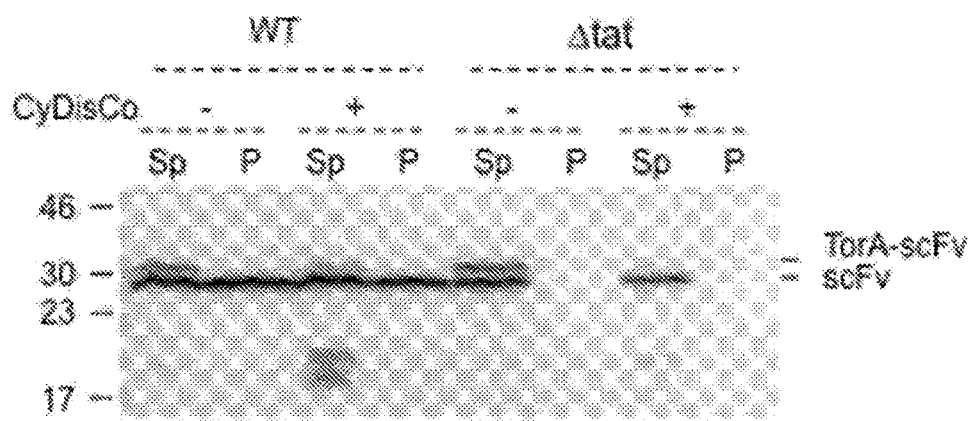
Figure 4A
Figure 4B
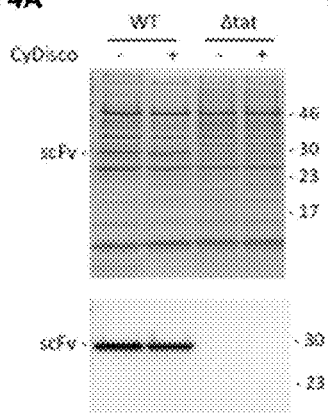
1   AQAAHMAEVQLVESGGSLVKPGGSLRLSC
31  AASGFTFSNYSMNWVRQAPGKGLEWISSI
68  SGSSRYIYYADFVKGRFTISRDNATNSLYLQ
106 MNSLRAEDTAVYYCVRSSITIFGGGMDVW
141 GRGTLVTVSSGGGGSGGGGSGGGGSQSVL
178 TQPASVSGSPGQSITISCAGTSSDVGGYNY
216 VSWYQQHPGKAPKLMIYEDSKRPSGVSNR
253 FSGSKSGNTASLTISGLQAEDEADYYCSSYT
182 TRSTRVFGGGTKLAVLGAAAEQKLISEEDLN
215 GAAHHHHHH (SEQ ID NO. 5).

BIOPHARMACEUTICAL PRODUCTION METHOD

The present invention relates to the production of disulphide bond-containing proteins and fragments in wild-type *Escherichia coli* by the Tat pathway.

*Escherichia coli* is a popular host for the production of recombinant proteins, underpinning the production of over a third of currently-licensed therapeutic proteins (Walsh (2010) *Drug Discov. Today* 15:773-780). There are several strategies for production of these biopharmaceuticals in *E. coli*, including expression of soluble proteins in the cytoplasm, expression as insoluble inclusion bodies or export to the periplasm followed by selective rupturing of the outer membrane to release the protein (Pierce et al (1997) *J. Biotechnol.* 58:1-11). The latter is a favoured approach for many protein products because it offers major advantages in downstream processing, including a reduction in the release of contaminant proteins and proteases, a lack of DNA release and less debris micronisation, hence better clarification performance (reviewed in Balasundaram et al (2009) *Trends Biotechnol.* 27:477-485; Harrison and Keshavarz-Moore (1996) *Ann. NY Acad. Sci.* 782:143-158). In addition, the periplasm is an oxidising environment which is essential for the production of disulphide bond-containing proteins. In wild type *E. coli* host strains, these cannot form in the cytoplasm.

Export of biopharmaceuticals to the periplasm is normally achieved by attachment of an N-terminal 'Sec'-type signal peptide which directs export via the general secretory (Sec) pathway (reviewed in Georgiou and Segatori (2005) *Curr. Opin. Biotechnol.* 16:538-545). This system transports protein substrates through a membrane-bound translocase in an unfolded form, after which the protein folds in the periplasm and any disulphide bonds are formed at this point. However, a high proportion of heterologous proteins are Sec-incompatible because they fold too rapidly, or too tightly, for the Sec pathway to handle effectively. In this context, the twin-arginine translocation (Tat) system offers a potentially important alternative to the Sec pathway. It operates in parallel with the Sec pathway in most bacteria but uses a completely different translocation mechanism. As with Sec substrates, Tat substrates are synthesised with N-terminal signal peptides, but these contain specific determinants including the presence of a highly conserved twin-arginine motif. The Tat pathway has two unique properties that have major implications for its exploitation.

First, it transports fully-folded proteins (for reviews see Miller and Klsgen (2005) *Mol. Membr. Biol.* 22:113-21; Robinson et al (2011) *Biochim. Biophys. Acta* 1808:876-874) and therefore has real potential for the export of proteins with folding properties that preclude Sec-dependent export. An example is green fluorescent protein (GFP), a tightly-folding protein that cannot normally be exported by Sec, but which is very efficiently exported by Tat (Thomas et al (2001) *Mol. Microbiol.* 39:47-53). Moreover, the Tat pathway can support levels of protein export that are comparable to those obtained in Sec-dependent industrial production systems; fed-batch fermentation studies showed that periplasmic GFP levels exceeded 1 g protein per liter culture (Matos et al (2014) *Biotech. Prog.* 30:281-290).

A second Tat trait is also highly relevant for biotechnological exploitation purposes: not only is Tat capable of exporting fully folded proteins, there is widespread evidence that it preferentially exports correctly folded proteins—even heterologous proteins. Indeed, studies on mutated versions of several substrates have shown an all-or-nothing effect, in that misfolded proteins are essentially 100% rejected (reviewed in Robinson et al (supra)). The underlying quality control mechanism is poorly understood but this trait is potentially important for biotechnological exploitation of Tat because it implies that exported products should have high specific activities and minimal heterogeneity.

While this trait has interesting implications for the use of Tat in production platforms, there is evidence that it may cause problems for the export of disulphide-bond requiring proteins. Several proteins which contain disulphide bonds in the native state could not be exported by Tat, because they were found to be misfolded, and hence completely Tat-incompatible, in the absence of cytoplasmic disulphide formation (DeLisa et al (2003) *Proc. Natl. Acad. Sci. USA* 100: 6115-6120; Matos et al 2014 (supra)). However, some proteins were exported in an *E. coli* mutant strain, Δgor/ΔtrxB, that allows formation of the disulphide bonds in the cytoplasm (DeLisa et al (supra)). Similar results were obtained by Matos et al when disulphide-requiring proteins were expressed in 'CyDisCo' strains that promote efficient formation of disulphide bonds in the cytoplasm (Matos et al 2014 (supra)). The Tat pathway thus clearly identified these constructs as misfolded in wild type strains and rejected them. Hence, Tat-dependent export required prior oxidative folding.

The CyDisCo set of strains has the ability to catalyse cytoplasmic disulphide bond formation and isomerisation and has been shown to enable the Tat-dependent export of two disulphide-requiring model proteins, namely PhoA and AppA. These results suggested that the strain has promise for the export of disulphide-requiring biopharmaceuticals and so a series of such proteins has been studied for export by the Tat pathway. While the results showed that the proteins are all efficiently exported in CyDisCo-expressing cells, a major surprise, however, was the finding that export is equally efficient in wild type cells. In the absence of CyDisCo, the proteins are shown to acquire disulphide bonds in the periplasm.

Accordingly, the present invention encompasses a method for the manufacture of a disulphide-requiring biopharmaceutical having an element of at least tertiary structure, preferably a substantially active and/or natural conformation, using wild type *E. coli*.

The method is particularly applicable to proteins and fragments thereof, such as antibody fragments.

In particular, the method comprises use of Tat-dependent export from the cytoplasm to the periplasm and subsequent extraction and purification. It is believed the exported proteins and fragments acquire disulphide bonds in the periplasm, indicating that the normal disulphide oxidation machinery in the bacterium is able to recognise and act on the proteins and fragments thereof.

The processes for extraction and purification of biopharmaceuticals, particularly proteins and fragments thereof, from bacteria are well known and it will be appreciated that any suitable methods and processes may be used.

The method is particularly suitable for the manufacture of proteins and fragments thereof containing at least one disulphide bond, preferably 2, 3 or 4 disulphide bonds, wherein some degree of folding of the proteins and fragments thereof is carried out in the cytoplasm without the formation of the disulphide bonds. Ideally, the proteins and fragments thereof adopt at least tertiary structures before the formation of disulphide bonds. It is believed that these tertiary structures are accepted as fully-folded by the Tat machinery.

In a preferred embodiment, the proteins and fragments thereof are able to fold into a substantially active and/or native or near-native conformation in the cytoplasm before the formation of disulphide bonds. In this way the proteins and fragments there of avoid rejection by the Tat pathway's proofreading system.

In a particularly preferred embodiment, the method is used for the manufacture of disulphide bond containing antibody fragments.

In a particular example, the method may be used for the manufacture of proteins and antibody fragments including two disulphide bonds.

In a further example, the method may be used for the manufacture of proteins and antibody fragments having a molecular weight of less than about 50 kDa, preferably a molecular weight of less than about 30 kDa, more preferably a molecular weight of about 20-30 kDa.

It will be appreciated that the present invention also encompasses disulphide-requiring biopharmaceuticals, such as proteins and fragments thereof, manufactured by any of the methods described above.

The present invention will now be described in more detail with reference to the following examples and figures in which:

FIG. 1 is an immunoblot showing the efficient Tat-dependent export of interferon alpha 2b (IFN) and human growth hormone (hGH) by Tat in both the presence and absence of CyDisCo components. hGH and IFN were expressed with a TorA Tat signal peptide in *E. coli* in the presence or absence of CyDisCo components. After 3 h, cells were separated into cytoplasm/membrane/periplasm fractions (C, M, P) and samples were immunoblotted to detect the proteins. Mobilities of mature-size hGH and IFN are indicated; the mobilities of molecular mass markers are indicated (in kDa) on the left.

Figure 2:
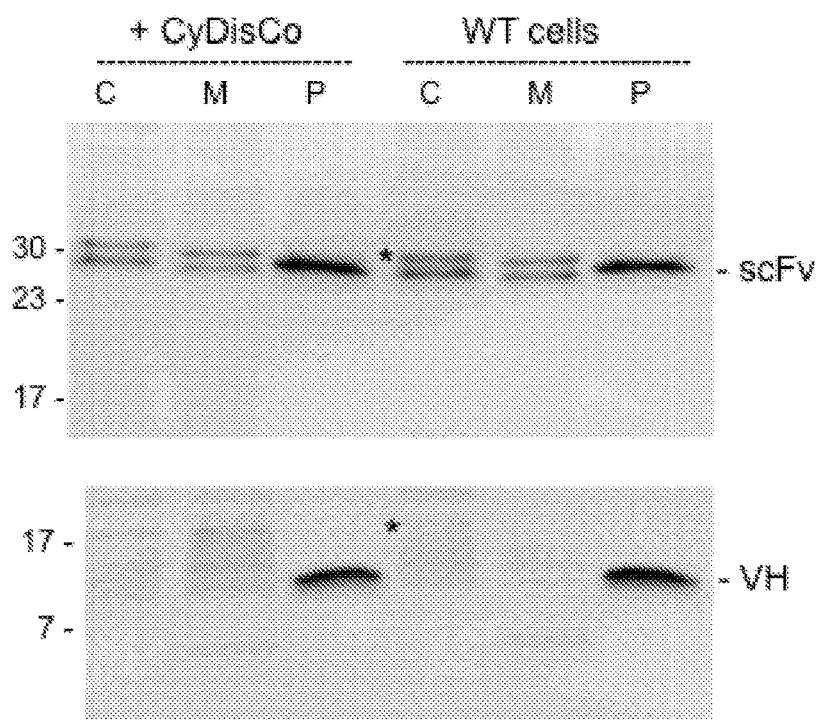

FIG. 2 is an immunoblot showing that scFv and VH domain antibody constructs are exported by Tat in the presence and absence of CyDisCo components. TorA-scFv and TorA-VH domain constructs were expressed in wild type or CyDisCo cells as described for IFN and hGH, and cells were fractionated to yield cytoplasm, membrane and periplasm samples (C, M, P). The samples were analysed by immunoblotting using antibodies to the His tag, and mobilities of mature scFv and VH domain protein are indicated. Asterisks denote the precursor proteins.

FIG. 3 is an immunoblot showing that export of TorA-scFv occurs exclusively by the Tat pathway. TorA-scFv was expressed in wild type and tat null mutant strains for 3 h, in either the presence or absence of CyDisCo components as indicated. After this period cells were fractionated and spheroplast and periplasm (Sp, P) samples were analysed by immunoblotting using antibodies to the C-terminal His tag on the scFv protein. The mobilities of the precursor and mature scFv forms are indicated.

Figure 5A:
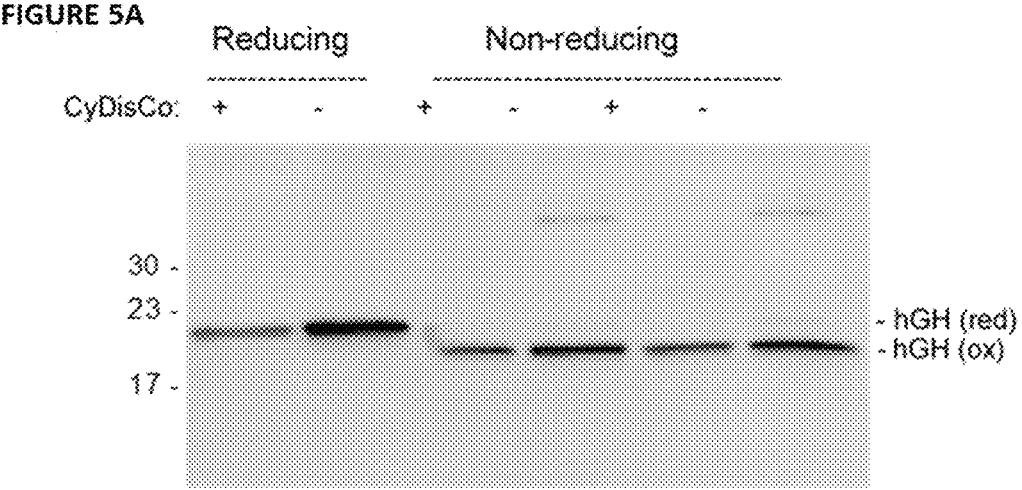
Figure 5B:
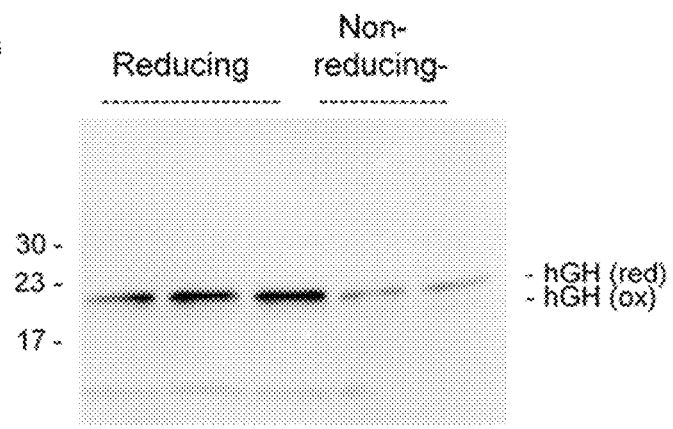

FIG. 4A-B illustrates that TorA-scFv is efficiently exported and accurately processed. FIG. 4A is an immunoblot showing that TorA-scFV was expressed in MC4100 cells or the tat null mutant strains in the presence or absence of CyDisCo components as indicated. The periplasmic fractions were run on Coomassie-stained gels and the putative scFv band (present in the periplasm of wild type cells but not tat null mutant cells) is indicated. FIG. 4B shows the full mature scFv sequence with the peptides identified by MS in bold and the sequence identified by MS/MS in bold and underlined. The putative scFv band from the CyDisCo-expressing sample was excised and subjected to MALDI TOF for peptide mass fingerprinting. FIG. 5A-B shows that periplasmic hGH is disulphide-bonded after Tat-dependent export in wild type or CyDisCo-expressing cells. FIG. 5A is an immunoblot showing that TorA-hGH was expressed in the presence or absence of CyDisCo components as indicated (+/−). The periplasmic fraction was subjected to SDS-polyacrylamide gel electrophoresis in the presence or absence of reducing agent (2-mercaptoethanol) as indicated. The mobilities of reduced and oxidised hGH (Red, Ox) are indicated, as is a higher band that is possibly a dimer. FIG. 5B is an immunoblot in which the same TorA-hGH construct was expressed in a dsbEr strain in the absence of CyDisCo components and samples of the periplasm fraction were again run under reducing or non-reducing conditions as in FIG. 5A. Mobilities of oxidised and reduced hGH forms are indicated (Ox, Red).

Figure 6:
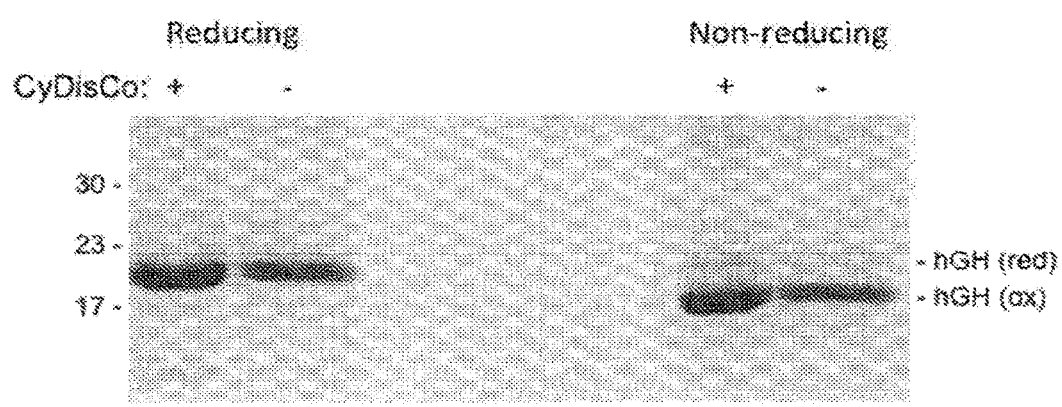

FIG. 6 shows immunoblots in which hGH is almost completely disulphide-bonded after purification from the periplasm of wild type or CyDisCo-expressing cells. TorA-hGH was expressed in wild type or CyDisCo-expressing cells and the protein was purified from periplasmic extracts by IMAC chromatography. The protein was run on SDS polyacrylamide gels in the presence or absence of 2-mercaptoethanol as indicated. Mobilities of oxidised and reduced forms are indicated.

Figure 7A:
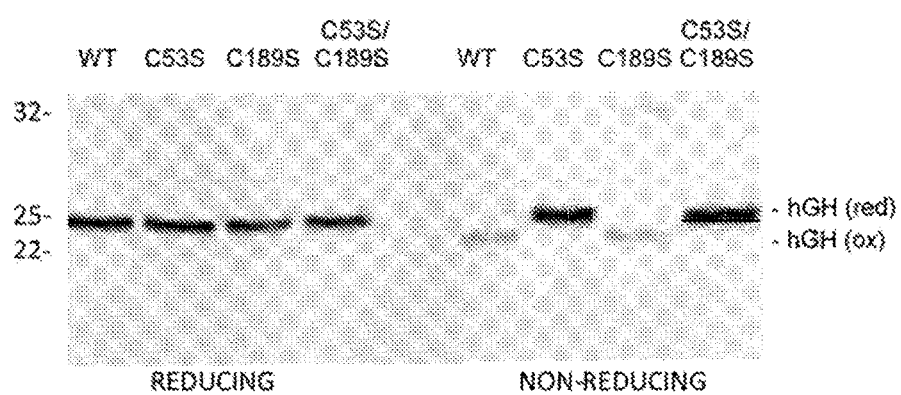
Figure 7B:
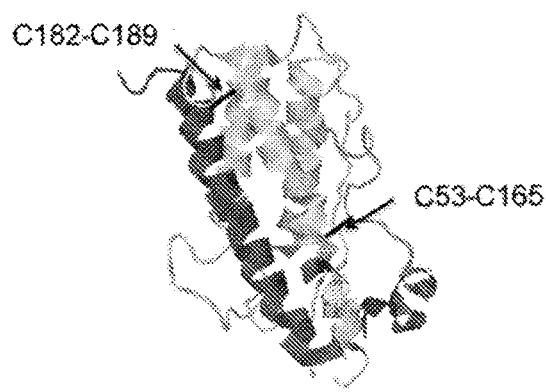

FIG. 7A-B shows that complete disruption of one or both disulphide bonds in hGH does not affect export by the Tat pathway. FIG. 7A is an immunoblot in which site-specific mutagenesis of TorA-hGH was carried out to substitute one of the Cys residues involved in the first or second disulphide bond (Cys53, Cys189, respectively) by serine. A third, double-mutant combined both substitutions. All three variants were expressed in wild type *E. coli* cells, together with non-mutated TorA-hGH, and the periplasmic fractions were isolated. These samples were run on SDS-polyacrylamide gels under reducing (left) or non-reducing (right) conditions. All of the mutated forms are clearly exported by Tat providing proof that prior disulphide bond formation is not required for export. FIG. 7B is a ribbon diagram of the hGH structure showing the positions of the disulphide bonds.

MATERIALS AND METHODS

Materials

All chemicals, unless specified otherwise, were obtained from Sigma Chemical Co. Ltd. (Poole, Dorset, UK) and were of analytical grade.

Plasmids & Bacterial Strains

All constructs were amplified using Phusion high fidelity DNA polymerase (New England Biolabs) to include a 5' NdeI site and a 3' BamHI site immediately after a 6-His tag. The product was then digested with NdeI and BamHI (New England Biolabs) and inserted into pYU49 which had been cut similarly (Matos et al., 2014).

All plasmid purification was performed using the QIAprep spin miniprep kit (Qiagen) and all purification from agarose gels was performed using the gel extraction kit (Qiagen), both according to manufacturer's instructions. All plasmids generated were fully sequenced (see Table 1 for plasmid names and details).

Growth Conditions

Following transformation, a single colony was used to inoculate 10 ml of LB media containing 100 μg mL$^{-1}$ ampicillin and grown overnight at 37° C., 200 rpm. Using the overnight culture, 50 ml of LB in 1L flasks containing appropriate antibiotics was inoculated to $OD_{600}$=0.05 and grown to approximately $OD_{600}$=0.5 at 37° C., 200 rpm. At $OD_{600}$=0.5, cells were induced with 1 mM IPTG and left for 3 hrs at 25° C. or 30° C. After this time an amount equivalent to 1 mL of $OD_{600}$=10 was collected by centrifugation (3,000 rpm, 10 minutes). The periplasmic fraction (P) was prepared by the EDTA/lysozyme/cold osmoshock procedure (Randall and Hardy (1986), Pierce et al (1997)). The pellet was then washed with buffer containing 50 mM Tris-Acetate (pH 8.2), 250 mM sucrose and 10 mM $MgSO_4$ and centrifuged for 5 minutes at 14,000 rpm, 4° C. The resulting pellet was then re-suspended in 50 mM Tris-Acetate, 2.5 mM EDTA (pH 8.2) and sonicated on ice for 4-6×10 seconds, 8 µm amplitude with 10 seconds between sonication (Soniprep 150plus, Sanyo Gallenkamp, Loughborough, UK). The sonicate was then centrifuged for 30 minutes at 70,000 rpm, 4° C. to collect the insoluble fraction. The supernatant was removed as the cytoplasmic fraction (C) and the pellet re-suspended in 50 mM Tris-Acetate, 2.5 mM EDTA (pH 8.2) to give the membrane/insoluble fraction (M). All cell fractions were stored frozen in aliquots for further experiments as repeated freeze-thawing can influence the results obtained in a protein-dependent manner.

Detection of Proteins by Immunoblotting

After SDS-PAGE and transfer, PVDF membranes to be immunoblotted with C-terminal His antibodies were blocked with PBS-T containing 5% (w/v) dried skimmed milk powder for at least 1 hour. The membranes were washed in PBS-T before incubation with PBS-T containing the primary antibody (Anti-His (C-term), Life Technologies, CA, USA) for 1 hour. The membranes were washed before incubation with the secondary antibody (Anti-Mouse IgG (H+L), HRP Conjugate, Promega, WI, USA) for another hour. The membranes were washed and immunoreactive bands were detected using ECL (enhanced chemiluminescence) kit (BioRad, Herts, UK) according to the manufacturer's instructions. Membranes were developed using a BioRad chemiluminescence imager and corresponding software.

Mass Spectrometry: In-Gel Digestion of Proteins

Excised, diced protein bands from Coomassie-stained SDS gels were washed, reduced and S-alkylated essentially as described in Fox et al ((2011) *J. Microbiol. Methods*. 84:243-250). A sufficient volume of 2 ng/µL of trypsin (modified sequencing grade, Promega, Southampton, UK) in 25 mM ammonium bicarbonate was added to cover the gel pieces and digestion performed overnight at 20° C. The digests were then acidified by the addition of a 0.5 volume of 50% acetonitrile with 5% formic acid prior to MS and MS-MS analysis.

MS and MS-MS Analysis

The sample (1 µL of the above peptide digest) was placed on the sample target (AnchorChip standard, 800 µm) and dried. Subsequently 0.5 µL of matrix was added and dried. The matrix was α-cyano-4-hydroxy-cinnamic acid (α-CHCA, 0.7 mg $mL^{-1}$ in 85% acetonitrile, 15% $H_2O$, 0.1% TFA and 1 mM $NH_4H_2PO_4$). For external calibration in the protein mass range, Peptide Calibration Standard I (Bruker) standards were used. MALDI TOF MS and MALDI TOF-TOF MS-MS analysis was performed (in the positive ion mode) using a Bruker UltrafleXtreme. The spectra were obtained in reflector mode with an acceleration voltage of 25 kV and a pulse ion extraction time of 80 ns. The mass range for MS was generally between 700 and 3500 m/z. The number of laser shots summed in MS was 3500. The number of laser shots summed in MS-MS was 3000. The software flexAnalysis (Bruker, Bremen, Germany) was used for peak picking prior to using the standard Mascot search engine. The peptide mass fingerprint was searched against the non-redundant Swiss-Prot protein database (all organisms) placed in the public domain by UNIProt and modified by the addition of sequences corresponding to the recombinant fusion proteins being studied in this manuscript. flexAnalysis takes advantage of the isotopic envelope available from high resolution MS-MS spectra in peptide identification. Mascot is available from Matrix Science Ltd, London, UK.

TABLE 1

Strains and constructs used in this study

| Strain/Plasmid | Description | Source/Reference |
|---|---|---|
| DH5α | F_—80lacZ_M15_(lacZYA-argF) U169 deoR recA1 endA1 hsdR17 (RK_, mk_) gal-phoA supE44 thi-1 gyrA96 relA1 | Invitrogen, Carlsbad, CA, USA |
| W3110 | F- mcrA mcrB IN(rrnD-rrnE)1 lambda– | ATCC, Manassas, VA, USA |
| MC4100, Ara$^R$ | AraR, FaraD139DlacU169 rpsL150 relA1 flB5301 deoC1 ptsF25 rbsR | Bolhuis et al (2000) *FEBS Letts*. 472: 88-92 |
| ΔTatABCDE, Ara$^R$ | Like MC4100 Ara$^R$; ΔtatABCDE | Wexler et al (2000) *J. Biol. Chem*. 275: 16717-16722, Bolhuis et al (2000) (supra) |
| K12, ΔdsbB | Δ(araD-araB)567 ΔLacZ4787(::rrnB-3) λ⁻ dsdB774::kan rph-1 Δ(rhaD-rhaB)568 hsdR514 | Baba et al (2006) *Mol. Syst. Biol*. 2: 2006.008 |
| BL21(DE3) | fhuA2 [lon] ompT gal (λ DE3) [dcm] ΔhsdS λ DE3 = λ sBamHIo ΔEcoRI-B int::(lacI::PlacUV5::T7 gene1) i21 Δnin5 | Miroux and Walker (1996) *J. Mol. Biol*. 260: 289-298 |
| pYU49 | pET23 based vector with pTac promoter expressing TorA$_{sp}$ IL-1β scFv, codon-optimised Erv1p and mature codon-optimised hPDI | Matos et al 2014 (supra) |
| pHAK1 | As above with mature hGH-6His replacing IL-1β scFv | This study |
| pHAK2 | As above with mature α2b IFN-6His replacing IL-1β scFv | This study |
| pHAK7 | As above with β-galactosidase scFv-6His replacing IL-1β scFv | This study, Martineau et al (1998) *J. Mol. Biol*. 280: 117-127 |
| pHAK12 | As above with VH domain-6His replacing IL-1β scFv | This study |
| pHAK14 | As pHAK1 but without Erv1p and PDI | This study |
| pHAK15 | As pHAK2 but without Erv1p and PDI | This study |
| pHAK17 | As pHAK7 but without Erv1p and PDI | This study |
| pHAK23 | As pHAK12 but without Erv1p and PDI | This study |
| pKWK1 | As pHAK1 with C53S mutation | This study |
| pKWK2 | As pHAK1 with C189S mutation | This study |
| pKWK3 | As pHAK1 with C53S C189S mutation | This study |

Site-Specific Mutagenesis hGH mutants were made using the Agilent site-directed mutagenesis protocol. The primers used for the C53S mutation were (5' to 3'): CCCCCAGACCTC-CCTCTCTTTCTCAGAGTCTATTCCGAC (SEQ ID NO:1) and GTCGGAATAGACTCTGAGAAAGA-GAGGGAGGTCTGGGGG (SEQ ID NO:2). For the C189S mutant the following primers were used: GTGGAGGGCA-GCTCTGGCTTCCATCATCATCATCATCAC (SEQ ID NO:3) and GTGATGATGATGATGATGGAAGCCA-GAGCTGCCCTCCAC (SEQ ID NO:4). For the double C53S C189S mutant, the C189S mutant was used as a template with the C53S primers (described above)

Results

IFN, hGH, an scFv and a VH Domain Construct are all Efficiently Exported by Tat in the Absence of Prior Disulphide Formation Previous studies (DeLisa et al (supra); Matos et al 2014 (supra)) showed that several disulphide-bonded proteins, including PhoA, a phytase AppA, an scFv construct and a Fab fragment, were exported in *E. coli* when a Tat signal peptide was present at the N-terminus, provided that disulphide formation could occur in the cytoplasm. In one case this was achieved by expression in Δgor/ΔtrxB cells. This strain passively enables the formation of disulphide bonds in proteins in the cytoplasm by the removal of the two naturally occurring reducing pathways (Prinz et al (1997) *J. Biol. Chem.* 272(25):15661-15667). In the other case the proteins were expressed in 'CyDisCo' strains that express a thiol oxidase and protein disulphide isomerase in the cytoplasm, actively promoting efficient disulphide bond formation. The same constructs were not exported in wild type strains, with the Tat pathway clearly identifying these constructs as 'inappropriately folded' and rejecting them.

The primary aim of this study was to test whether the Tat system can export other disulphide-bonded therapeutic proteins with high efficiency and human growth hormone (hGH), human interferon α2b (IFN), an scFv raised against the omega peptide of β-galactosidase (described in Martineau et al (1998) *J. Mol. Biol.* 280:117-127) and an antibody VH domain construct (Dudgeon et al (2008) *Prot. Eng. Des. Sel.* 22:217-220) were chosen as targets. Constructs containing C-terminal His tags were used to aid identification of the proteins and all proteins bore N-terminal TorA signal peptides (as used in Matos et al 2014 (supra)) to direct export by the Tat pathway. The precursor proteins were expressed on a pET23-based plasmid either alone or together with the CyDisCo components Erv1p and mature human PDI.

FIG. 1 shows the results of export assays using TorA-hGH and TorA-IFN. After a 3 h induction of expression, the cells were fractionated to yield cytoplasm, membrane and periplasm samples (C, M, P) which were immunoblotted using antibodies to the His tags on the target proteins. The figure shows that most of the TorA-IFN is exported to the periplasm (P) and processed to the mature size (20.7 kDa). A small amount of precursor protein is apparent in the membrane fraction and some mature-size protein is also present in the cytoplasm. This is commonly found during export of Tat substrates, probably because the signal peptide is prone to proteolytic clipping (see e.g. Matos et al (2012) *Biotechnol. Bioeng.* 109:2533-2542). The export of TorA-hGH is even more efficient with the vast majority of protein being found in the periplasm and the precursor form being barely detectable in the cytoplasm.

FIG. 1 also shows similar assays carried out in wild type cells, i.e. in the absence of CyDisCo components. Surprisingly, export of both proteins is again highly efficient and both proteins are found predominantly in the periplasm as mature size proteins. Next, the export of the scFv and VH domain constructs were tested and the results of export assays in wild type and CyDisCo strains are shown in FIG. 2. The data again show efficient export of both substrates in that a substantial proportion of the scFv and the majority of the VH domain construct are found in the periplasm in both CyDisCo-expressing and wild type cells.

TorA-scFv is Exported Exclusively by the Tat Pathway

The data shown in FIGS. 1 and 2 are surprising because the Tat-dependent export of other disulphide-bonded proteins has shown an absolute dependence on prior cytoplasmic disulphide bond formation, as explained above. Therefore it was considered possible that the substrates tested in this study may in fact be exported by the Sec pathway, since Sec-type signal peptides are similar in overall structural terms to Tat signal peptides. To test this possibility directly, some of the same constructs were expressed in tat null mutant cells and the data for TorA-scFv are shown in FIG. 3.

The results show that the scFv is not exported in the tat mutant strain to any significant extent, either in the absence or presence of CyDisCo components. Indeed, all of the protein is found in the cytoplasm or membrane fractions (C, M). In control assays, export is again observed in both wild type and CyDisCo-expressing strains, confirming that the export observed in FIGS. 1 and 2 can be attributed solely to the Tat pathway. Identical results were obtained for TorA-IFN and the TorA-VH domain protein (data not shown).

TorA-scFv is efficiently exported and accurately processed to the mature size. The immunoblots shown in FIGS. 1 and 2 show that the four proteins appear to be exported with high efficiency by the Tat pathway, in the sense that the majority of detected protein is in the periplasm. In order to assess the actual export flux, and to additionally test whether the proteins are correctly processed to the mature size, the samples were analysed by Coomassie staining of the periplasm and mass spectrometry of the exported scFv. FIG. 4A shows a Coomassie-stained gel of the periplasmic fractions after export of TorA-scFv in wild type MC4100 cells or the tat null mutant strain, in either the presence or absence of CyDisCo components. The immunoblot (lower panel) shows that the scFv protein is present in the periplasm of the wild type cells and the Coomassie-stained gel (upper panel) shows that this corresponds to an abundant 28 kDa protein that is absent from the periplasm of the tat mutant strain. The presumed scFv band was excised and subjected to trypsin digestion and MALDI TOF as described in Materials and Methods. This generated the peptide sequences shown in FIG. 4B which confirm the protein to be scFv. Importantly, the N-terminal peptide sequences correspond precisely to the sequences immediately following the predicted signal peptidase cleavage site, with no evidence of incorrect processing or large-scale proteolytic clipping. These results provide strong evidence that the precursor protein is accurately processed to the mature size following export to the periplasm, and the relative abundance of the exported scFv, after only a 3 h export assay, shows that the protein is exported at a high rate in both the presence and absence of CyDisCo components.

Tat-Exported hGH and scFv Acquire Disulphide Bonds in the Periplasm

The four test proteins tested in this study are clearly exported by Tat in the absence of disulphide bond formation and the next study tested whether one of the proteins acquires disulphide bonds in the periplasm. The DsbABCD system catalyses disulphide bond formation in the periplasm (reviewed in Kadokura and Beckwith (2010) *Antioxid. Redox Signal* 13:1231-1246), usually with proteins that have been exported by the Sec pathway in an unfolded state. In contrast, the Tat pathway almost certainly exports proteins in either a fully folded or near-native state and under such circumstances it is by no means clear whether the Dsb system can access the required thiol groups in order to catalyse disulphide bond oxidation. This issue was investigated by analysis of the periplasmic proteins on reducing vs non-reducing SDS polyacylamide gels—disulphide-bonded proteins usually migrate differently under non-reducing conditions because the presence of disulphide bonds prevents full SDS-dependent unfolding of the proteins.

FIG. 5A shows immunoblots of periplasmic hGH after export in CyDisCo-expressing or wild type cells. The samples were run under reducing or non-reducing conditions (the latter samples were run in duplicate in case reducing agent diffused to the adjacent lane). hGH run under non-reducing conditions clearly migrates faster than the fully reduced sample, confirming that this protein sample contains disulphide bonds. Importantly, the vast majority of the protein from both CyDisCo and wild type cells runs with this increased mobility (denoted 'hGH (ox)'), confirming the presence of disulphide bonds and providing strong evidence that hGH exported in wild type cells acquires disulphide bonds in the periplasm. A small proportion of the protein runs further up the gel, possibly indicating formation of some dimer under these conditions.

It seemed likely that the exported, reduced hGH would acquire disulphide bonds using the DsbABCD machinery that catalyses disulphide bond formation in exported Sec substrates and this was tested using the same approaches. TorA-hGH was expressed in a dsbB⁻ strain that was previously used to study disulphide bond formation in other exported substrates (Matos et al 2014 (supra)) and the data are shown in FIG. 5B. In the absence of CyDisCo, hGH is exported and the samples migrate as the usual 19 kDa band under reducing conditions ('hGH (red)'). Importantly, the samples still run primarily with the same mobility under non-reducing conditions, with only a minority migrating more rapidly like the oxidised form (hGH (ox)). These data have been interpreted to indicate that, in the absence of DsbB, the bulk of the exported hGH is unable to form disulphide bonds properly, strongly suggesting that the DsbABCD machinery catalyses the formation of the bonds in the experiment shown in FIG. 1. A minor proportion of exported hGH does appear to contain disulphide bonds, and it is speculated that these may form as a result of spontaneous oxidation.

Larger amounts of hGH were also purified from periplasmic samples after export in CyDisCo and wild type cells. The protein was then analysed under reducing and non-reducing conditions. FIG. 6 shows that the purified hGH samples from CyDisCo and wild type cells both run as the expected 19 kDa band on reducing gels, whereas the faster-migrating form (containing disulphide bonds) was observed under non-reducing conditions. Importantly, the latter form predominates to an equal extent after purification from either wild type or CyDisCo cells, showing that the periplasmic protein can become essentially fully folded and disulphide-bonded whether the disulphide bonds are formed in the cytoplasm or periplasm. Taken together, the data from FIGS. 5 and 6 indicate that the Tat system can export these proteins even when they lack disulphide bonds and that these bonds can form after entry into the periplasm.

The Tat System can Transport hGH Even when Disulphide Bond Formation is Blocked by Substitution of the Cys Residues Involved The above studies imply that the Tat system is transporting a range of substrates in a reduced form, possibly because they are able to attain a near-native structure in the absence of disulphide bond formation. This is an important issue and it was considered important to confirm that a substrate can definitely be transported in the absence of prior disulphide formation. To do this site-specific mutagenesis was used to block disulphide bond formation in the hGH substrate. hGH contains two disulphide bonds: one between Cys53 and Cys165 (a long-range bond between residues remote from each other in sequence), and the other between Cys182 and Cys189 (a short range bond) (FIG. 7A). Substitution of Cys53 by serine (variant C53S) prevents formation of the first bond whereas substitution of Cys189 by serine (C189S) blocks formation of the second. Export of the C53S and C189S single mutants, together with the C53S/C189S double mutant, was tested and the data are shown in FIG. 7. The positions of the above disulphide bonds in hGH are also illustrated.

The blot shows periplasmic samples from the export assays and the reduced samples (on the left) show the presence of very similar levels of exported periplasmic protein in each case. None of the substitutions adversely affect translocation competence. Analyses of the samples under non-reducing conditions are shown on the right hand side of the Figure. The wild type protein shows the characteristic increase in mobility that accompanies disulphide bond formation and the same increase in mobility is observed with the C189S mutant. On the other hand, the C53S and double mutant do not show this increase in mobility and instead migrate with the same mobility as the reduced samples. From this it may be concluded that the first disulphide bond (disrupted in C53S) is solely responsible for the shift in mobility in SDS polyacrylamide gels whereas disruption of the second bond (in C189S) does not have a significant effect. This is consistent with the protein structure (FIG. 7B). The C182-C189 disulphide bond is a short-range bond whereas the C53S-Cys165 bond is a long range bond that effectively ties together distant regions of the protein. It is therefore unsurprising that the presence of this bond has a major effect on protein mobility when the sample is run under denaturing, non-reducing conditions. Notably, the Tat system exports all these variants and thus appears to recognise the proteins as correctly folded, despite the absence of one or both disulphide bonds.

Discussion

A number of previous reports (DeLisa et al (supra); Matos et al 2008 *EMBO J.* 27: 2055-2063; Matos et al 2014 (supra)) have shown that the Tat system has an effective, although poorly understood, quality control system that enables it to identify and reject proteins that are misfolded. This feature is important for the normal functioning of the system: many of its substrates are cofactor-containing proteins and it is important that these are only exported in a folded, assembled state. However, the feature does not only operate during the export of natural Tat substrates, since this selectivity operates towards a variety of heterologous proteins when expressed with Tat signal peptides, including some mammalian disulphide-bonded proteins.

The Tat pathway has considerable potential for the industrial production of biopharmaceuticals, since it is known to be capable of exporting a number of 'Sec-incompatible' proteins and is furthermore capable of exporting them at high rates in fermenter systems (Matos et al 2012 (supra)). Moreover, the inbuilt quality control feature should enable the system preferentially to export proteins that are correctly folded, which is a potentially valuable trait for biotechnological applications. It was believed that the export of disulphide-bonded proteins would be problematic since these cannot form native structures in the cytoplasm, but recent studies have shown that CyDisCo strains offer potential as a means of presenting the Tat system with prefolded, disulphide-bonded substrates that it can export to the periplasm (Matos et al 2014 (supra)). The main aim of the present study was to determine whether this CyDisCo-Tat combination could be used for the production of other disulphide-bonded proteins, especially biotherapeutics.

This issue was approached by testing for export of human interferon α2b, hGH, an scFv and a VH domain construct. It has been shown that all are exported by the Tat system with high efficiency. Indeed, the export efficiencies observed with some of these substrates are higher than those observed with many native Tat substrates, despite expressing these heterologous substrates at relatively high levels using pET23-based plasmids. However, the major surprise from this study is that none of these substrates require prior disulphide bond formation for export: the proteins are all exported with similar, usually undiminished, efficiencies in wild type cells where the reducing cytoplasm prevents disulphide bond formation prior to export. The likely explanation is that the proteins adopt structures that are sufficiently native-like to be accepted by the Tat system's proofreading system. Indeed, one of the substrates, hGH, is known to adopt a near-native structure in the absence of disulphide bond formation and is even active in this state (Youngman et al (1995) *J. Biol. Chem.* 270:19816-19822; Bewley et al (1969) *Biochemistry* 8, 4701-4708).

These experiments were carried out in a very similar manner to those described in Matos et al 2014 (supra) and the question is why this set of substrates shows such differing requirements for export. Without wishing to be bound by theory, it is believed that the most likely reason relates to the complexity of the proteins studied in previous reports by DeLisa et al (supra) and Matos et al 2014 (supra). PhoA is a 51 kDa protein with two sequential disulphide bonds, while AppA is a 53 kDa protein with 4 disulphide bonds. The dimeric Fab construct studied in the DeLisa et al (supra) report is particularly complex with both intra-chain and inter-chain disulphide bonds. In contrast, the proteins tested in the present study are smaller, with molecular masses of 20.7 kDa (IFN), 23.6 kDa (hGH), 28.9 kDa (scFv) and none contain more than two disulphide bonds. One possibility is that the simpler 3-dimensional structure of the proteins enables them to acquire native, or near-native, structures in the absence of disulphide bond formation.

Finally, the data have implications for the mechanism of the Tat proofreading system. While this system has a remarkable ability to detect whether substrates are folded, it is clearly not perfect and the four substrates analysed in this study were able to 'fool' the translocation pathway and undergo transport. The first point is that the Tat system clearly cannot detect whether disulphide bonds have formed in substrates, at least in these proteins. The second point is that, assuming that all four substrates are not 100% correctly folded in the absence of disulphide bond formation, there appears to be some margin for error in the proofreading mechanism.

The invention claimed is:

1. A method for the manufacture of a disulphide-requiring biopharmaceutical protein having an element of at least tertiary structure using wild type *E. coli*, the method comprising:
   a) culturing wild type *E. coli* transformed with a plasmid expressing the biopharmaceutical with an N-terminal TorA signal peptide;
   b) inducing the *E. coli* to express the biopharmaceutical protein; and
   c) obtaining the biopharmaceutical protein from a periplasmic fraction, wherein:
   the biopharmaceutical protein comprises no more than two disulphide bonds and has a molecular weight of less than 30 kDa, and
   the element of at least tertiary structure is adopted in the cytoplasm of the wild type *E. coli*.

2. The method of claim 1, wherein the method comprises use of twin-arginine translocation (Tat)-dependent export from the cytoplasm to the periplasm and subsequent extraction and purification.

3. The method of claim 1, wherein the disulphide-requiring biopharmaceutical protein is an antibody fragment.

4. The method of claim 1, wherein the disulphide-requiring biopharmaceutical protein is manufactured with a substantially active and/or natural conformation.

5. The method of claim 1, wherein the disulphide-requiring biopharmaceutical protein adopts at least a tertiary structure before the formation of disulphide bonds.

6. The method of claim 1, wherein the disulphide-requiring biopharmaceutical protein folds into a substantially active and/or native or near-native conformation in the cytoplasm before the formation of disulphide bonds.

7. The method of claim 1, wherein the plasmid is a pET23-based plasmid.

* * * * *

SEQUENCE LISTING

<160> NUMBER OF SEQ ID NOS: 5

<210> SEQ ID NO 1
<211> LENGTH: 39
<212> TYPE: DNA
<213> ORGANISM: Artificial Sequence
<220> FEATURE:
<223> OTHER INFORMATION: DNA Primer sequence

<400> SEQUENCE: 1
cccccagacc tccctctctt tctcagagtc tattccgac                              39

<210> SEQ ID NO 2
<211> LENGTH: 39
<212> TYPE: DNA
<213> ORGANISM: Artificial Sequence
<220> FEATURE:
<223> OTHER INFORMATION: DNA Primer sequence

<400> SEQUENCE: 2
gtcggaatag actctgagaa agagagggag gtctggggg                              39

<210> SEQ ID NO 3
<211> LENGTH: 39
<212> TYPE: DNA
<213> ORGANISM: Artificial Sequence
<220> FEATURE:
<223> OTHER INFORMATION: DNA Primer sequence

<400> SEQUENCE: 3
gtggagggca gctctggctt ccatcatcat catcatcac                              39

<210> SEQ ID NO 4
<211> LENGTH: 39
<212> TYPE: DNA
<213> ORGANISM: Artificial Sequence
<220> FEATURE:
<223> OTHER INFORMATION: DNA Primer sequence

<400> SEQUENCE: 4

```
gtgatgatga tgatgatgga agccagagct gccctccac                          39

<210> SEQ ID NO 5
<211> LENGTH: 277
<212> TYPE: PRT
<213> ORGANISM: Artificial Sequence
<220> FEATURE:
<223> OTHER INFORMATION: Synthetic Polypeptide

<400> SEQUENCE: 5

Ala Gln Ala Ala His Met Ala Glu Val Gln Leu Val Glu Ser Gly Gly
1               5                   10                  15

Ser Leu Val Lys Pro Gly Gly Ser Leu Arg Leu Ser Cys Ala Ala Ser
                20                  25                  30

Gly Phe Thr Phe Ser Asn Tyr Ser Met Asn Trp Val Arg Gln Ala Pro
            35                  40                  45

Gly Lys Gly Leu Glu Trp Ile Ser Ser Ile Ser Gly Ser Ser Arg Tyr
        50                  55                  60

Ile Tyr Tyr Ala Asp Glu Val Lys Gly Arg Phe Thr Ile Ser Arg Asp
65                  70                  75                  80

Asn Ala Thr Asn Ser Leu Tyr Leu Gln Met Asn Ser Leu Arg Ala Glu
                85                  90                  95

Asp Thr Ala Val Tyr Tyr Cys Val Arg Ser Ser Ile Thr Ile Phe Gly
            100                 105                 110

Gly Gly Met Asp Val Trp Gly Arg Gly Thr Leu Val Thr Val Ser Ser
        115                 120                 125

Gly Gly Gly Gly Ser Gly Gly Gly Ser Gly Gly Gly Gly Ser Gln
130                 135                 140

Ser Val Leu Thr Gln Pro Ala Ser Val Ser Gly Ser Pro Gly Gln Ser
145                 150                 155                 160

Ile Thr Ile Ser Cys Ala Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Asp Ser Lys Arg Pro Ser Gly Val Ser Asn Arg Phe Ser
        195                 200                 205

Gly Ser Lys Ser Gly Asn Thr Ala Ser Leu Thr Ile Ser Gly Leu Gln
210                 215                 220

Ala Glu Asp Glu Ala Asp Tyr Tyr Cys Ser Ser Tyr Thr Thr Arg Ser
225                 230                 235                 240

Thr Arg Val Phe Gly Gly Gly Thr Lys Leu Ala Val Leu Gly Ala Ala
            245                 250                 255

Ala Glu Gln Lys Leu Ile Ser Glu Glu Asp Leu Asn Gly Ala Ala His
            260                 265                 270

His His His His His
        275
```